(12) United States Patent  
Omura

(10) Patent No.: US 9,121,805 B2  
(45) Date of Patent: Sep. 1, 2015

(54) RADIATION GENERATING APPARATUS, RADIOGRAPHING APPARATUS, AND COMPUTER READABLE STORAGE MEDIUM STORING PROGRAM

(71) Applicant: CANON KABUSHIKI KAISHA, Tokyo (JP)

(72) Inventor: Satoru Omura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/226,620

(22) Filed: Mar. 26, 2014

(65) Prior Publication Data  
US 2014/0291539 A1 Oct. 2, 2014

(30) Foreign Application Priority Data  
Mar. 29, 2013 (JP) ................... 2013-073016

(51) Int. Cl.  
*A61B 6/00* (2006.01)  
*G01N 23/00* (2006.01)  
*A61B 6/10* (2006.01)

(52) U.S. Cl.  
CPC .............. *G01N 23/00* (2013.01); *A61B 6/4405* (2013.01); *A61B 6/447* (2013.01); *A61B 6/4429* (2013.01); *A61B 6/547* (2013.01); *A61B 6/107* (2013.01)

(58) Field of Classification Search  
CPC .............................. A61B 6/4405; A61B 6/447  
See application file for complete search history.

(56) References Cited

U.S. PATENT DOCUMENTS

| | | | | |
|---|---|---|---|---|
| 4,501,557 A * | 2/1985 | Tamura et al. | ................... | 433/79 |
| 4,752,948 A * | 6/1988 | MacMahon | .................... | 378/198 |
| 5,067,145 A * | 11/1991 | Siczek et al. | ................... | 378/198 |
| 2004/0109530 A1* | 6/2004 | Amitani et al. | .................. | 378/37 |
| 2010/0001156 A1* | 1/2010 | Stefan | ......................... | 248/274.1 |
| 2011/0243309 A1* | 10/2011 | Weijiang | ....................... | 378/197 |
| 2011/0249806 A1* | 10/2011 | Wendlandt et al. | ............ | 378/198 |
| 2011/0249807 A1* | 10/2011 | Dirisio et al. | ................. | 378/198 |
| 2014/0098943 A1* | 4/2014 | Omura et al. | .................. | 378/198 |
| 2014/0133627 A1* | 5/2014 | Sakuragi et al. | ................ | 378/62 |
| 2014/0291539 A1* | 10/2014 | Omura | ........................... | 250/393 |

FOREIGN PATENT DOCUMENTS

JP 2007-144161 A 6/2007

* cited by examiner

*Primary Examiner* — Thomas R Artman  
(74) *Attorney, Agent, or Firm* — Canon USA Inc. IP Division

(57) ABSTRACT

A radiation generating apparatus and a radiographing apparatus configured to allow a radiation generating unit to be installed at arbitrary positions include an arm configured to support a radiation generating unit that generates radiation, a pillar configured to rotatably support the arm, and a movable base configured to support the pillar and move on a floor surface are provided, and the arm includes an expandable mechanism configured to expand and contract in a longitudinal direction of the arm.

21 Claims, 11 Drawing Sheets

RADIATION GENERATING APPARATUS, RADIOGRAPHING APPARATUS, AND COMPUTER READABLE STORAGE MEDIUM STORING PROGRAM

BACKGROUND OF THE INVENTION

1. Field of the Invention

This disclosure relates to a radiographing apparatus having a radiation generating unit configured to generate radiation toward an object.

2. Description of the Related Art

Examples of a radiographing apparatus of the related art include a portable radiographing apparatus. When performing photography by using the portable radiographing apparatus, a supporting portion configured to allow installation of a radiation generating unit at a sufficiently high position and allow installation of the radiation generating unit at a position aligned with a portion to be photographed of an object is required.

Accordingly, an arm configured to support the radiation generating unit and a pillar configured to support the arm are formed into a clamping structure. (Japanese Patent Application Laid-Open No. 2007-144161)

However, in the radiographing apparatus disclosed in Japanese Patent Application Laid-Open No. 2007-144161, a movable range of the radiation generating unit depends on the length of the arm. Therefore, an improvement to allow installation of the radiation generating unit at arbitrary positions is desired.

SUMMARY OF THE INVENTION

This disclosure is directed to a radiographing apparatus configured to allow installation of the radiation generating unit at arbitrary positions. Accordingly, as disclosed herein, the radiographing apparatus includes an expandable arm configured to support a radiation generating unit which generates radiation, a pillar configured to support the arm, and a movable base configured to support the pillar and move on a floor surface.

Further features of the present invention will become apparent from the following description of exemplary embodiments with reference to the attached drawings.

DESCRIPTION OF THE EMBODIMENTS

Referring now to the attached drawings, preferred embodiments of this disclosure will be described.

Example 1

Figure 1B:
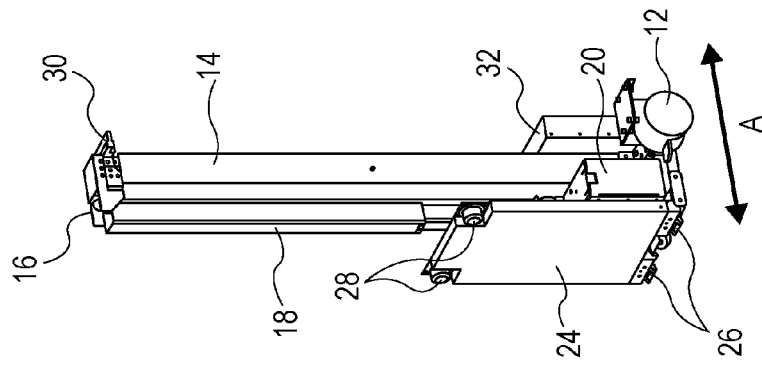
FIGS. 1A and 1B are drawings illustrating a general configuration of a radiation generating apparatus in operating and transporting modes, respectively.
Figure 1A:
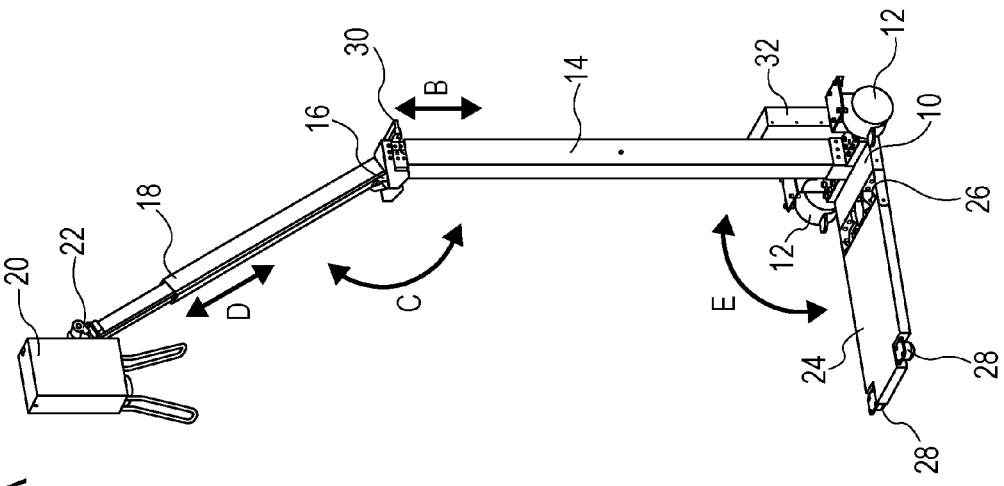

FIGS. 1A and 1B are drawings illustrating a configuration of a radiation generating apparatus of Example 1. FIG. 1A illustrates a perspective view of the radiation generating apparatus at the time of photography (operating mode). FIG. 1B is a perspective view of the radiation generating apparatus at the time of transportation (transportation mode).

The radiation generating apparatus includes a movable base 10 having wheels 12 installed thereon, a pillar 14 extending upright in a perpendicular direction with respect to the movable base 10, an expandable arm 18 configured to be installed so as to be rotatable with respect to the pillar 14, a radiation generating unit 20 installed rotatably with respect to the arm 18 and configured to generate radiation, and a supporting platform 24 configured to be foldable with respect to the movable base 10. In order to make the radiation generating apparatus compact as much as possible, a mode of the radiation generating apparatus having no display apparatus configured to display images will be described here.

The movable base 10 includes the wheels 12 configured to rotate with respect to a floor surface. The wheels 12 are a plurality of tires or casters, and are always placed on the floor surface. In the mode illustrated in FIG. 1B, the radiation generating apparatus may be moved together with the movable base 10 in a fore-and-aft direction (direction A) by rotating the wheels 12.

The pillar 14 is secured to the movable base 10. The pillar 14 is provided on the movable base 10 so as to extend upright in the perpendicular direction. The pillar 14 has a predetermined length and includes an expandable mechanism configured to expand and contract in a longitudinal direction of the pillar 14. In other words, the pillar 14 is expandable in the perpendicular direction (direction B).

The shape of the pillar 14 is not limited to a straight shape as illustrated in FIGS. 1A and 1B, and may have a curved shape instead. The pillar 14 may be composed of an aggregation of a plurality of members, for example, an aggregation of bar members, an aggregation of cylindrical members, and an aggregation of linear members (net structure). In other words, the pillar 14 may have any configuration as long as the arm 18 is rotatably supported.

The pillar 14 has the handle 30 configured to be gripped by an operator who transports the radiation generating apparatus. As illustrated in FIG. 1, a handle 30 is installed on an upper end of the pillar 14. The operator is allowed to move the movable base 10 and transport the radiation generating apparatus by gripping the handle 30 and pulling the same in a direction of travel of the movable base 10. Since the handle 30 is installed at the upper end of the pillar 14, when the pillar 14 is expanded or contracted in the perpendicular direction (direction B), the handle 30 also moves in the perpendicular direction (direction B). In other words, the position of the handle 30 may be adjusted by expansion and contraction of the pillar 14.

As illustrated in FIG. 1A, the pillar 14 is provided with a control unit 32 installed thereon, which is configured to control exposure of the radiation generating unit 20. The pillar 14 is provided with the control unit 32 installed at a lower end thereof, and the pillar 14 and the control unit 32 are integrated. The control unit 32 may be installed on the movable base 10. The control unit 32 is installed on the pillar 14 on the same side as the handle 30. The control unit 32 is composed of relatively heavy components. The balance of the radiation generating apparatus may be stabilized by installing the control unit 32 at the lower end of the pillar 14 (on the side closer to the movable base 10 or the floor surface). The control unit 32 may have a power source unit configured to supply a power source to the radiation generating unit 20.

The arm 18 is coupled at one end thereof to the radiation generating unit 20, and at the other end thereof to the pillar 14. The arm 18 supports the radiation generating unit 20, and has a predetermined length. As illustrated in FIG. 1A, the arm 18 has the expandable mechanism configured to expand and contract in a longitudinal direction of the arm 18 (direction D). In other words, the radiation generating unit 20 may be moved in the longitudinal direction of the arm 18 (direction D). In this mode, the arm 18 is expanded in a predetermined direction of expansion (direction D) and allows the radiation generating unit 20 to protrude toward the object.

The shape of the arm 18 is not limited to a straight shape as illustrated in FIGS. 1A and 1B and may have a curved shape instead. The arm 18 may be composed of an aggregation of a plurality of members, for example, an aggregation of bar members, an aggregation of cylindrical members, and an aggregation of linear members (net structure). In other words, the arm 18 may have a configuration to support the radiation generating unit 20. A detailed example of the expandable mechanism of the arm 18 will be described later.

The arm 18 is allowed to rotate about the upper end of the pillar 14. Specifically, as illustrated in FIG. 1A, the pillar 14 includes an arm hinge portion 16 configured to allow the arm 18 to rotate in a predetermined direction of rotation (direction C). The arm 18 has a rotatable range at a predetermined angle with respect to the predetermined direction of rotation (direction C) (for example, approximately 180°). The arm 18 is configured to be bent to a side opposite to the side where the handle 30 and the control unit 32 are installed.

The arm hinge portion 16 has a mechanism which couples the arm 18 and the pillar 14, and allows the arm 18 to be opened and closed with respect to the pillar 14. When the arm 18 is folded, the arm 18 is brought into a state of being substantially parallel to the pillar 14.

In this manner, the arm hinge portion 16 allows the arm 18 to deform the mode thereof from a form in which the arm 18 extends upward or sideward illustrated in FIG. 1A to a form in which the arm 18 is stored together with the radiation generating unit 20 illustrated in FIG. 1B by being rotated in the predetermined direction of rotation (direction C). The form in which the arm 18 extends upward or sideward illustrated in FIG. 1A is a state in which the radiation generating unit 20 is protruded toward the object. The form in which the arm 18 is stored together with the radiation generating unit 20 illustrated in FIG. 1B is a state in which the arm 18 is folded and the arm 18 extends in substantially parallel to the pillar 14. In other words, the form in which the arm 18 is stored together with the radiation generating unit 20 is a state in which the radiation generating unit 20 is arranged at the position closest to the floor surface.

A rotating portion 22 configured to rotate the radiation generating unit 20 is installed between the radiation generating unit 20 and the arm 18. By rotating the radiation generating unit 20, the radiation generating unit 20 is positioned with respect to the object, and radiation may be directed to a desired direction. A detailed example of the rotating portion 22 will be described later.

The supporting platform 24 is a component configured to support the radiation generating apparatus. Although the components that come into contact with the floor surface in the radiation generating apparatus are only the wheels 12 of the movable base 10 in the form illustrated in FIG. 1B, the components that come into contact with the floor surface in the radiation generating apparatus are the wheels 12 of the movable base 10 and the supporting platform 24 in the form illustrated in FIG. 1A. The wheels 12 of the movable base 10 and the supporting platform 24 support the radiation generating apparatus. The supporting platform 24 contributes to increase the surface area of the radiation generating apparatus coming into contact with the floor surface. Therefore, even when the radiation generating unit 20 is positioned with respect to the object, for example, the radiation generating apparatus is balanced by the supporting platform 24.

Specifically, the supporting platform 24 is a plate-shaped member in the form of a raised level surface, and has leg portions 28 configured to support the radiation generating apparatus in a state of being in contact with the floor surface. The supporting platform 24 has a surface area larger than any side surfaces of the radiation generating unit 20. The leg portions 28 are installed on a bottom surface of the supporting platform 24. The leg portions 28 may be movable mechanisms such as a plurality of tires or casters configured to move on the floor surface. The supporting platform 24 is configured to be foldable in a predetermined direction of rotation (direction E) with respect to the movable base 10. The supporting platform 24 is configured to rotate in a direction opposite to the pillar 14. The supporting platform 24 has a rotatable range of approximately 90° with respect to the predetermined direction of rotation (direction E). The axis of rotation of the supporting platform 24 is parallel to the axis of rotation of the arm 18.

Specifically, the supporting platform 24 is coupled to the movable base 10 via a supporting leg hinge portion 26. The supporting leg hinge portion 26 allows the supporting platform 24 to be folded. At the time of photography, the operator opens the supporting platform 24 and supports the radiation generating apparatus by the supporting platform 24 and the movable base 10 as illustrated in FIG. 1A. At this time, the supporting platform 24 is integrated with the movable base 10 by the supporting leg hinge portion 26. The supporting leg hinge portion 26 includes a lock mechanism configured to couple and fix the supporting platform 24 and the movable base 10.

At the time of transportation, the operator firstly stores the arm 18 together with the radiation generating unit 20 as illustrated in FIG. 1B. Then, the lock between the supporting platform 24 and the movable base 10 by the supporting leg hinge portion 26 is released to close the supporting platform 24. Since the supporting platform 24 is larger than the radiation generating unit 20, a mode in which the supporting platform 24 covers the radiation generating unit 20 results. Since the supporting platform 24 has a surface area larger than those of any side surfaces of the radiation generating unit 20, the mode in which the supporting platform 24 covers the radiation generating unit 20 results. In other words, when the supporting platform 24 and the arm 18 are folded, the mode in which the supporting platform 24 covers the radiation generating unit 20 results.

The radiation generating unit 20 is a transmissive radiation generating unit. The transmissive radiation generating unit blocks radiation other than those necessary, and hence radiation shielding members are arranged on the electron incoming side and a radiation emitting side of a target. The transmissive radiation generating unit needs not to be covered with shielding members such as lead over the entire periphery of a radiation generating tube or an envelope in which the radiation generating tube is stored. Therefore, a compact and light-weight structure is achieved in comparison with a rotating anode radiation generating unit, for example. Therefore, the supporting platform 24 serves as a cover of the radiation generating unit 20 to protect the radiation generating unit 20. When the supporting platform 24 and the arm 18 are folded, all the components of the radiation generating apparatus are arranged on the movable base 10. Therefore, the radiation generating apparatus is supported only by the movable base 10.

At the time of transportation (when the supporting platform 24 and the arm 18 are folded), heavy components of the radiation generating unit 20 and the control unit 32 are arranged at positions near the floor surface, so that the center of gravity of the radiation generating apparatus may be lowered. Accordingly, the balance of the radiation generating apparatus may be maintained, and an operating force of the handle 30 for inclining the radiation generating apparatus at the time of transportation may be reduced.

Figure 2:
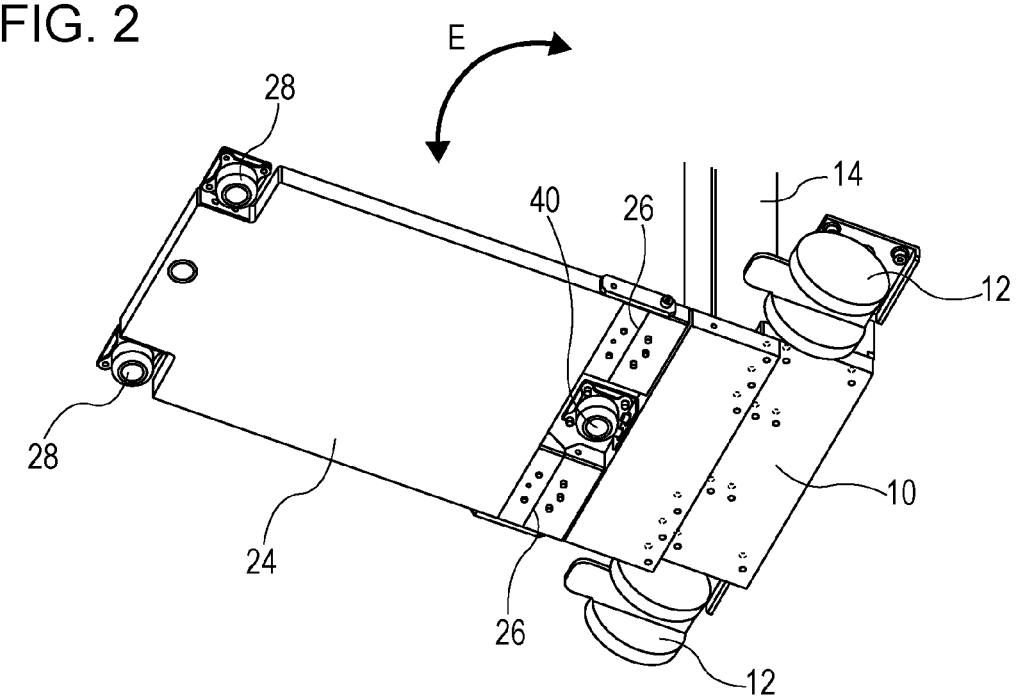
FIG. 2 is a drawing illustrating a bottom or base surface of the radiation generating apparatus of this disclosure.

FIG. 2 is a drawing mainly illustrating bottom surfaces of the movable base 10 and the supporting platform 24. The wheels 12 are installed at both ends of the movable base 10. Each of the wheels 12 has a lock mechanism configured to stop the rotation thereof.

The movable base 10 includes a leg portion 40 configured to come into contact the floor surface and support the apparatus in addition to the wheels 12. The leg portion 40 may be a movable mechanism such as a plurality of tires or casters.

The leg portions 28 are installed on the bottom surface of the supporting platform 24. As illustrated in FIG. 2, when the supporting platform 24 is opened, the radiation generating apparatus is supported by the leg portions 28 of the supporting platform 24 and the wheels of the movable base 10. At this time, the radiation generating apparatus is supported by four points including two of the leg portions 28 and two of the wheels 12.

The eradiation generating unit 20 is a transmissive radiation generating unit, and hence a compact and light-weight structure is achieved in comparison with the rotating anode radiation generating unit. Therefore, a heavy carriage for balancing the radiation generating unit 20 is no longer necessary. Even with the foldable supporting platform 24, the radiation generating apparatus is balanced. The radiation generating unit 20 is the transmissive radiation generating unit, and hence the radiation generating unit 20 may be arranged between the pillar 14 and the supporting platform 24. As illustrated in FIG. 1B, when the supporting platform 24 is folded, the radiation generating apparatus is supported by the leg portions 40 of the movable base 10 and the wheels 12 of the movable base 10. At this time, the radiation generating apparatus is supported at three points including one leg portion 40 and two of the wheels 12.

In a state in which the supporting platform 24 is deployed, all of at least two leg portions 28 and the wheels 12 of the movable base 10 need to be in contact with the floor surface, and the leg portion 40 does not have to be in contact with the floor surface. Since the leg portion 40 simply has to be a contact point at the time of transportation, the leg portion 40 may be a projecting portion.

Figure 3:
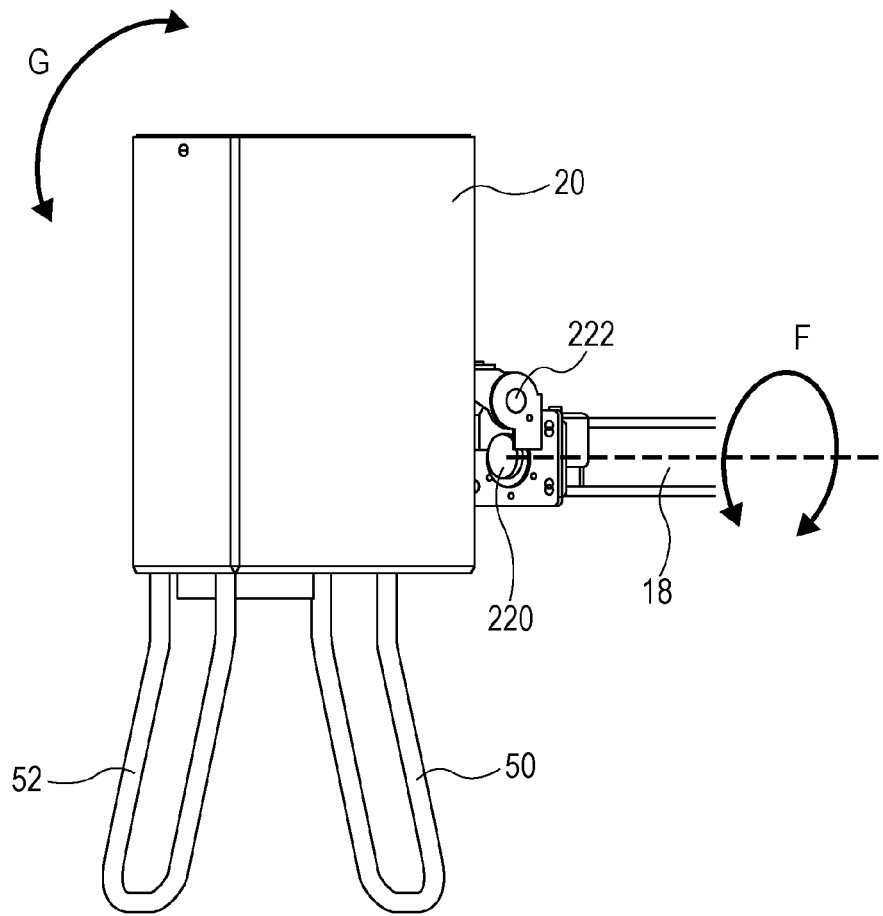
FIG. 3 is a drawing illustrating a rotating portion of the radiation generating apparatus of this disclosure.

FIG. 3 is a detailed explanatory drawing of the rotating portion 22 that rotates the radiation generating unit 20. The rotating portion 22 includes a swivel hinge 220 configured to rotate the radiation generating unit 20 about an axis parallel to the longitudinal direction of the arm 18, and a tilt hinge 222 configured to rotate the radiation generating unit 20 about an axis perpendicular to the longitudinal direction of the arm 18. In the rotating portion 22, the swivel hinge 220 is installed on the arm 18 side, and the tilt hinge 222 is installed on the radiation generating unit 20 side.

With the swivel hinge 220, the radiation generating unit 20 may be rotated in a predetermined direction of rotation (direction G). As regards a direction of irradiation of the radiation generating unit 20, the arm 18 is allowed to rotate at least the radiation generating unit 20 within a range from −90° to +90° with reference to a case where the direction of irradiation of the radiation generating unit 20 is directed toward the floor surface a state in which the arm 18 extends horizontally.

With the tilt hinge 222, the radiation generating unit 20 may be rotated in a predetermined direction of rotation (direction F). The axis of rotation in the direction F, which is an axis of rotation of the tilt hinge 222, matches a center axis of the arm 18. The axis of rotation of the swivel hinge 220 in the direction G and the axis of rotation of the tilt hinge 222 in the direction F extend orthogonally to each other. By rotating the radiation generating unit 20 by the tilt hinge 222, the radiation generating unit 20 may be inclined to an angle in which the direction of irradiation of the radiation generating unit 20 is directed toward the floor surface irrespective of the angle of the arm 18 with respect to the pillar 14.

When moving from the position of the radiation generating unit 20 at the time of photography illustrated in FIG. 1A to the position of the radiation generating unit 20 at the time of the transportation illustrated in FIG. 1B, the radiation generating unit 20 is rotated by the swivel hinge 220 and the tilt hinge 222. Therefore, the radiation generating unit 20 may be stored between the pillar 14 and the supporting platform 24. When the arm 18 is folded to store the radiation generating unit 20, the direction of generation of radiation of the radiation generating unit 20 is the horizontal direction.

The swivel hinge 220 and the tilt hinge 222 may be operated independently. The swivel hinge 220 and the tilt hinge 222 are preferably a torque hinge configured to retain the posture of the radiation generating unit 20 as desired. For example, these hinges may be a combination of torque hinges having a small torque or damper hinges having a lock mechanism configured to fix a given angle of hinge opening. Furthermore, a lock mechanism configured to fix the radiation generating unit 20 only at a desired posture may also be installed.

Figure 4:
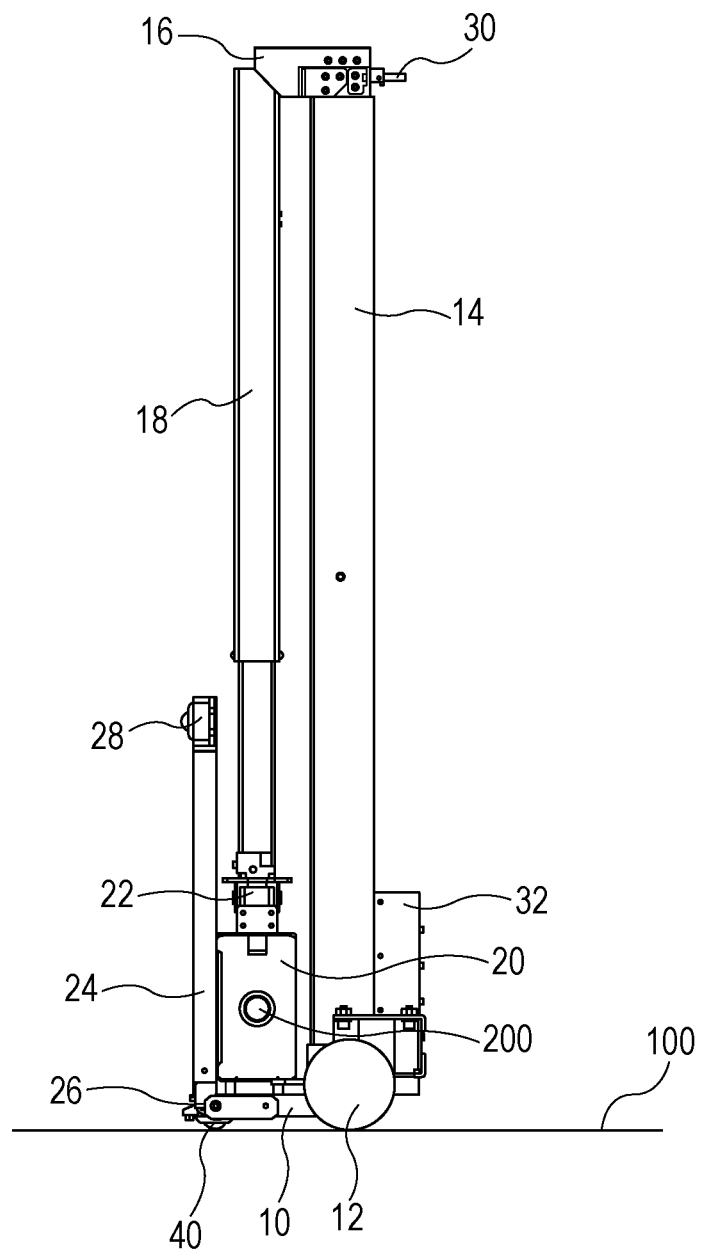
FIG. 4 is a drawing illustrating a storage mode of the radiation generating apparatus of this disclosure.
Figure 5:
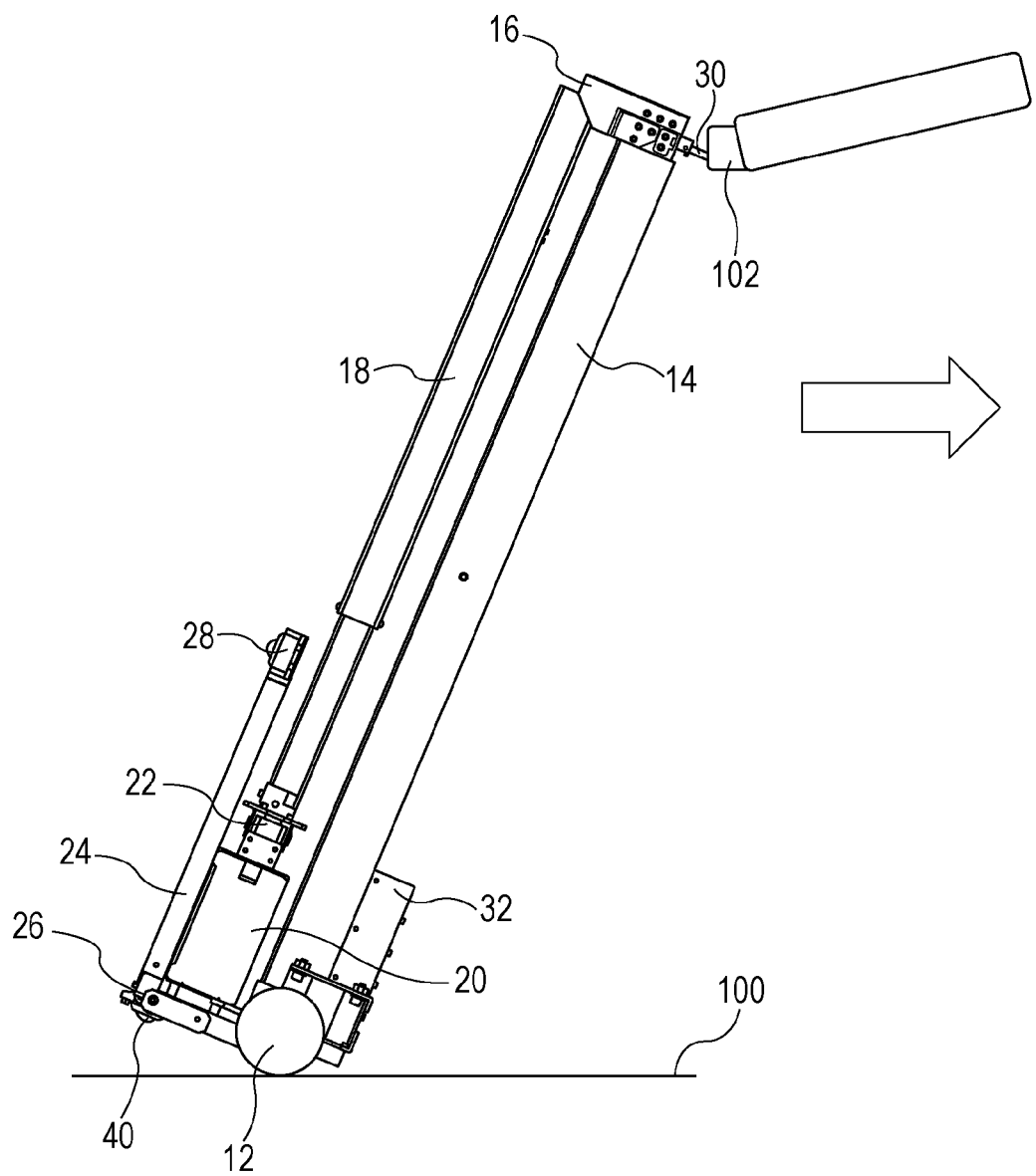
FIG. 5 is a drawing illustrating a transporting mode of the radiation generating apparatus of this disclosure.

The radiation generating unit 20 includes a guide portion 50 and a guide portion 52 as auxiliary portions configured to maintain a distance between the radiation generating unit 20 and the object constant. The operator is allowed to move the radiation generating unit 20 to a desired position by gripping the guide portion 50 or the guide portion 52 and lifting or pulling the guide portion 50 or the guide portion 52. FIG. 4 is a drawing illustrating a storage mode of the radiation generating apparatus. FIG. 5 is a drawing illustrating a transportation form of the radiation generating apparatus. As illustrated in FIG. 4, the arm 18 is folded to store the radiation generating unit 20 at the time of the transportation. The radiation generating unit 20 is arranged between the pillar 14 and the supporting platform 24. The center of gravity of the radiation generating unit 20 is positioned in the vicinity of the movable base 10, and is positioned in the vicinity of a floor surface 100. Here, the center of gravity of the radiation generating unit 20 is indicated by a point 200.

The center of gravity 200 of the radiation generating unit 20 at the time of transportation is configured to be arranged in an upper air on the inside of a polygonal shape having vertices at contact points between the wheels 12 of the movable base 10 and the floor surface of the leg portion 40.

In a horizontal direction (a lateral direction in FIG. 4) in the direction of travel of the movable base 10, the radiation generating unit 20 is arranged between the leg portion 40 and the wheels 12 of the movable base 10. On the movable base 10, the supporting platform 24, the supporting platform 24 and the arm 18, the pillar 14, and the control unit 32 are arranged from the left in this order. The arm 18 and the pillar 14 are components relatively longer than other components which constitute the radiation generating apparatus. The radiation generating apparatus may be balanced by storing the arm 18 and the pillar 14 at a center portion of the movable base 10 and clamping the arm 18 and the pillar 14 between the supporting platform 24 and the control unit 32.

The radiation generating unit 20 and the control unit 32 are components relatively heavier than other components which constitute the radiation generating apparatus. The radiation generating apparatus may be balanced by arranging the radiation generating unit 20 and the control unit 32 in the vicinity of the floor surface 100 when the radiation generating unit 20 is stored.

When the arm 18 is folded and the radiation generating unit 20 is stored, the center of gravity of the arm 18 and the radiation generating unit 20 is arranged between the leg portion 40 and the wheels 12 of the movable base 10. In the perpendicular direction, the radiation generating unit 20 is arranged on the movable base 10. The center of gravity of the pillar 14 is arranged between the leg portion 40 and the wheels 12 of the movable base 10.

When the arm 18 is folded and the radiation generating unit 20 is stored, the pillar 14, the arm 18, the supporting platform 24 extend substantially parallel to each other. The length of the pillar 14 is longer than the lengths of the arm 18 and the radiation generating unit 20. Therefore, when the arm 18 is folded to store the radiation generating unit 20, the radiation generating unit 20 is prevented from colliding with the movable base 10.

At the time of transportation, in a state in which the radiation generating apparatus stands upright as illustrated in FIG. 4, the operator firstly releases the lock mechanism configured to stop the rotation of the wheels 12. Then, the operator grips the handle 30 with a hand 102. As illustrated in FIG. 5, the operator pulls the handle 30 in a direction that the operator wants to move the radiation generating apparatus. Here, a mode in which the handle 30 is pulled rightward is illustrated. At this time, the radiation generating apparatus is inclined and only the wheels 12 of the movable base 10 are in contact with the floor surface, so that the wheels 12 rotate. By the rotation of the wheels 12, the radiation generating apparatus may be moved rightward.

When the radiation generating apparatus is moved to a desired position, the operator releases his or her hand 102 that has been gripping the handle 30. As illustrated in FIG. 4, the radiation generating apparatus is brought into an upright position.

Figure 6:
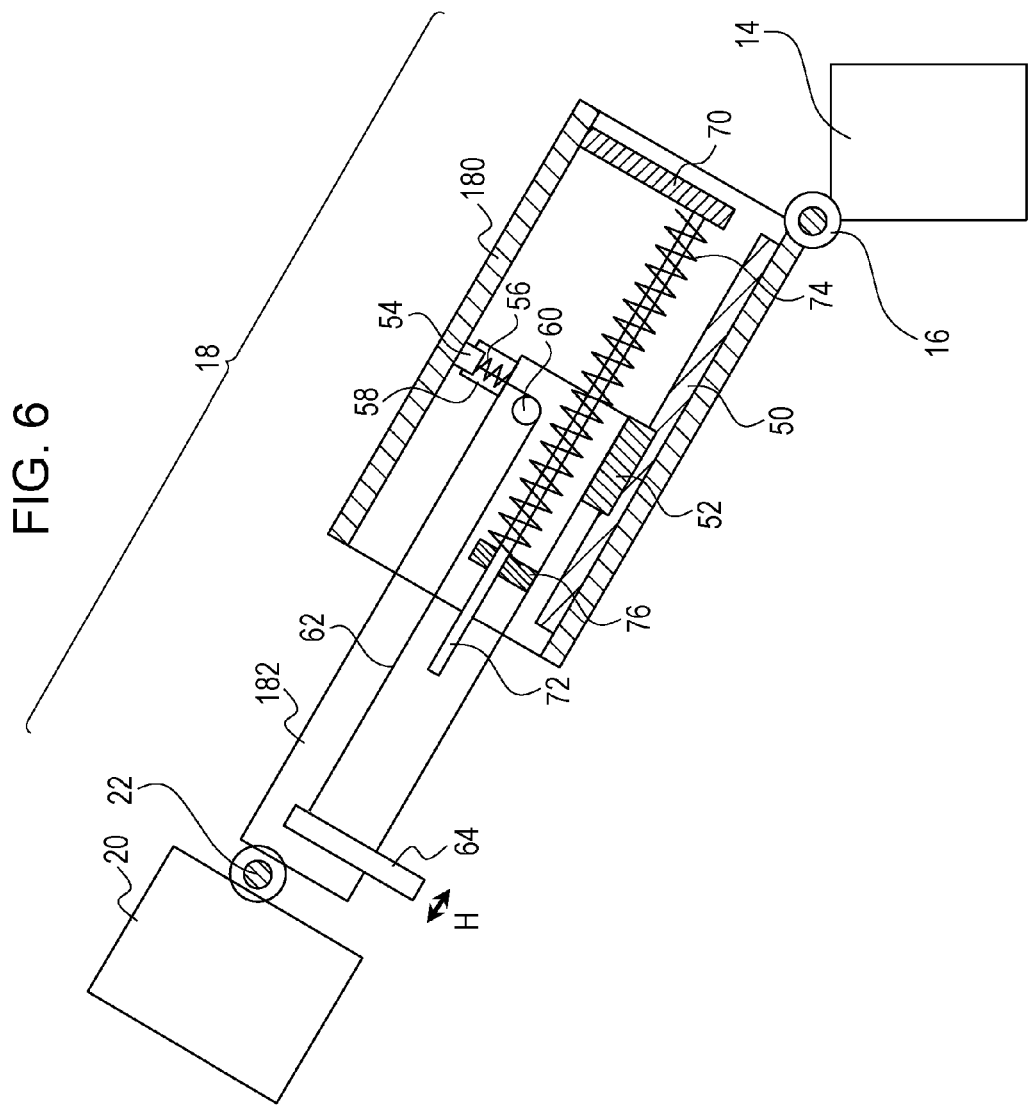
FIG. 6 is a drawing illustrating an expandable mechanism of an arm of the radiation generating apparatus of this disclosure.

FIG. 6 is a drawing illustrating an expandable mechanism of the arm 18 of the radiation generating apparatus. A detailed example of the expandable mechanism of the arm 18 will be described with reference to FIG. 6. FIG. 6 illustrates a cross section of the arm 18. The arm 18 includes a fixed arm 180, and a movable arm 182 configured to be movable with respect to the fixed arm 180. The fixed arm 180 and the movable arm 182 are both hollow and have the same cross-sectional shape. The cross section of the fixed arm 180 is one size larger than the cross section of the movable arm 182, and part of the movable arm 182 is arranged inside the fixed arm 180. The fixed arm 180 and the movable arm 182 have a so-called nest structure.

The fixed arm 180 is provided on the pillar 14 side, and the movable arm 182 is provided on the radiation generating unit 20 side. The fixed arm 180 is coupled to the pillar 14 via the arm hinge portion 16, and does not expand and contract with respect to the pillar 14. The movable arm 182 expands and contracts with respect to the fixed arm 180.

The fixed arm 180 has a linear guide rail 50 which functions as a guide for causing a sliding portion 52 of a movable arm 182, which will be described later, to move linearly installed thereon. The linear guide rail 50 is installed inside the fixed arm 180. The movable arm 182 includes the sliding portion 52 configured to move on the linear guide rail 50 installed thereon. The sliding portion 52 is installed outside the movable arm 182. The sliding portion 52 engages the linear guide rail 50 and moves linearly along the linear guide rail 50. The sliding portion 52 engages the linear guide rail 50, thereby supporting the movable arm 182 with respect to the fixed arm 180.

In this manner, the movable arm 182 is expanded and contracted with respect to the fixed arm 180 by the linear movement of the sliding portion 52 on the linear guide rail 50. Examples of other expandable mechanisms include a combination of a cam follower and a guide rail, or a rack and pinion. The stroke of the movable arm 182 is determined by the length of the linear guide rail 50. In other words, the stroke of the movable arm 182 depends on the length of the linear guide rail 50. Therefore, by adjusting the length of the linear guide rail 50, the stroke of the movable arm 182 may be adjusted. For example, when the length of the sliding portion 52 is assumed to be 100 mm, if the length of the linear guide rail 50 is 300 mm, the stroke of the movable arm 182 may be 200 mm. At this time, the length of expansion and contraction of the arm 18 is 200 mm. If the length of the linear guide rail 50 is 600 mm, the stroke of the movable arm 182 may be 500 mm. At this time, the length of expansion and contraction of the arm 18 is 500 mm.

The movable arm 182 includes a slide guide 58 configured to position the movable arm 182 installed thereon. The slide guide 58 on the movable arm 182 is installed on a side opposite to the sliding portion 52 that moves on the linear guide rail 50. The slide guide 58 is arranged outside the movable arm 182 that is arranged inside the fixed arm 180. In other words, even though the movable arm 182 is moved, the slide guide 58 of the movable arm 182 is arranged always inside the fixed arm 180.

The slide guide 58 includes a lock member 54 configured to restrain the movement of the movable arm 182 by coming into contact with the inside of the fixed arm 180, and a compression spring 56 configured to press the lock member 54 against the inside of the fixed arm 180. The lock member 54 is configured to project from the slide guide 58. The lock member 54 is formed of a material having a high coefficient of static friction, for example, a rubber or a metal. The compression spring 56 is applicable instead if it is a mechanism configured to press the lock member 54 against (resilient member).

The movable arm 182 includes a lock release handle 64 configured to release the lock by the lock member 54. The lock release handle 64 can be slid in the longitudinal direction (direction H) of the movable arm 182. By releasing the lock by the lock member 54 by the lock release handle 64, the movable arm 182 is allowed to move. In other words, the arm 18 may be expanded and contracted.

Specifically, a pulley 60 and a wire 62 are installed for releasing the lock by the lock member 54 via the lock release handle 64 in the interior of the movable arm 182. The wire 62 is coupled to the lock member 54 and the lock release handle 64 via the pulley 60. The wire 62 from the lock release handle 64 to the pulley 60 is arranged in the interior of the movable arm 182. The wire 62 coupled to the lock release handle 64 reaches the pulley 60 along the longitudinal direction of the movable arm 182 and the pulley 60 redirects the wire 62. In the movable arm 182, a portion where the movable arm 182 and the slide guide 58 come into contact with each other includes a hole portion which allows the wire 62 to pass through. The wire 62 is bent in the direction orthogonal to the direction of the axis of the movable arm 182 by the pulley 60, and is coupled to the lock member 54 through the hole portion. Accordingly, the lock release handle 64 and the lock member 54 are interlocked with each other.

Although the compression spring 56 presses the lock member 54 against the inside of the fixed arm 180, the lock release handle 64 moves toward the radiation generating unit 20 and the lock is released, whereby pressure of the lock member 54 against the fixed arm 180 is released. The lock member 54 is no longer in contact with the inside of the fixed arm 180, the arm 18 is then free to expand and contract. In this manner, the lock of the movable arm 182 may be released by the operator operating the lock release handle 64. At this time, the length of the arm 18 may be set to an arbitrary length. When the lock release handle 64 is returned to its original position, the lock member 54 is pressed against the fixed arm 180 by the compression spring 56, so that the movable arm 182 is locked and expansion and contraction of the arm 18 are stopped.

At the time of photography, the arm 18 is directed obliquely upward, and the radiation generating unit 20 may be arranged at a position higher than the pillar 14 as illustrated in FIG. 6. When the arm 18 is expanded and the radiation generating unit 20 is installed obliquely upward, the operator lifts the radiation generating unit 20 together with the movable arm 182.

Then, the arm 18 has a biasing mechanism configured to alleviate an operating force of the operator in expansion and contraction of the arm 18. The biasing mechanism is a mechanism that applies a force mainly in the direction in which the arm 18 expands. As an example of the biasing mechanism, the arm 18 includes a spring member 74 configured to apply a force in the direction of expansion of the arm 18. The biasing mechanism is not limited to the spring member 74, and may be a hydraulic mechanism or a resilient member such as rubber, and may be a mechanism that alleviates the operating force of the operator.

The direction that the spring member 74 expands is the same as the direction that the arm 18 expands (the longitudinal direction of the arm 18). As the biasing mechanism, the spring member 74 coupled the movable arm 182 and the fixed arm 180 is provided.

Specifically, a spring fixing portion 70 configured to fix one end of the spring member 74 is installed inside the fixed arm 180. The spring fixing portion 70 is a fixing plate projecting from inside the fixed arm 180. A spring fixing portion 76 configured to fix the other end of the spring member 74 is installed inside the movable arm 182. The spring fixing portion 76 is a fixing plate projecting from inside the movable arm.

A spring shaft 72 of the spring member 74 is secured to the spring fixing portion 70 installed on the fixed arm 180 together with the spring member 74. The axial direction of the spring shaft 72 corresponds to the direction in which the arm 18 expands (the longitudinal direction of the arm 18).

The spring fixing portion 76 installed on the movable arm 182 is a spring bearing configured to guide the spring shaft 72. The spring fixing portion 76 is configured to guide the spring shaft 72 so as to slide in the direction in which the arm 18 expands (the longitudinal direction of the arm 18). The spring fixing portion 76 installed on the movable arm 182 has a hole portion which allows the spring shaft 72 to penetrate therethrough. The spring shaft 72 penetrates through the hole portion of the spring fixing portion 76 and is allowed to be inserted and taken out from the spring fixing portion 76.

The spring member 74 is arranged so as to cover part of the spring shaft 72, and is configured to be placed between the spring fixing portion 76 installed on the movable arm 182 and the spring fixing portion 70 installed on the fixed arm 180 from both sides. In other words, the spring member 74 is coupled to the movable arm 182 and the fixed arm 180. Therefore, when the operator lifts the radiation generating unit 20 together with the movable arm 182 and expands the movable arm 182 with respect to the fixed arm 180, the operating force of the operator is reduced by the spring member 74.

Figure 7:
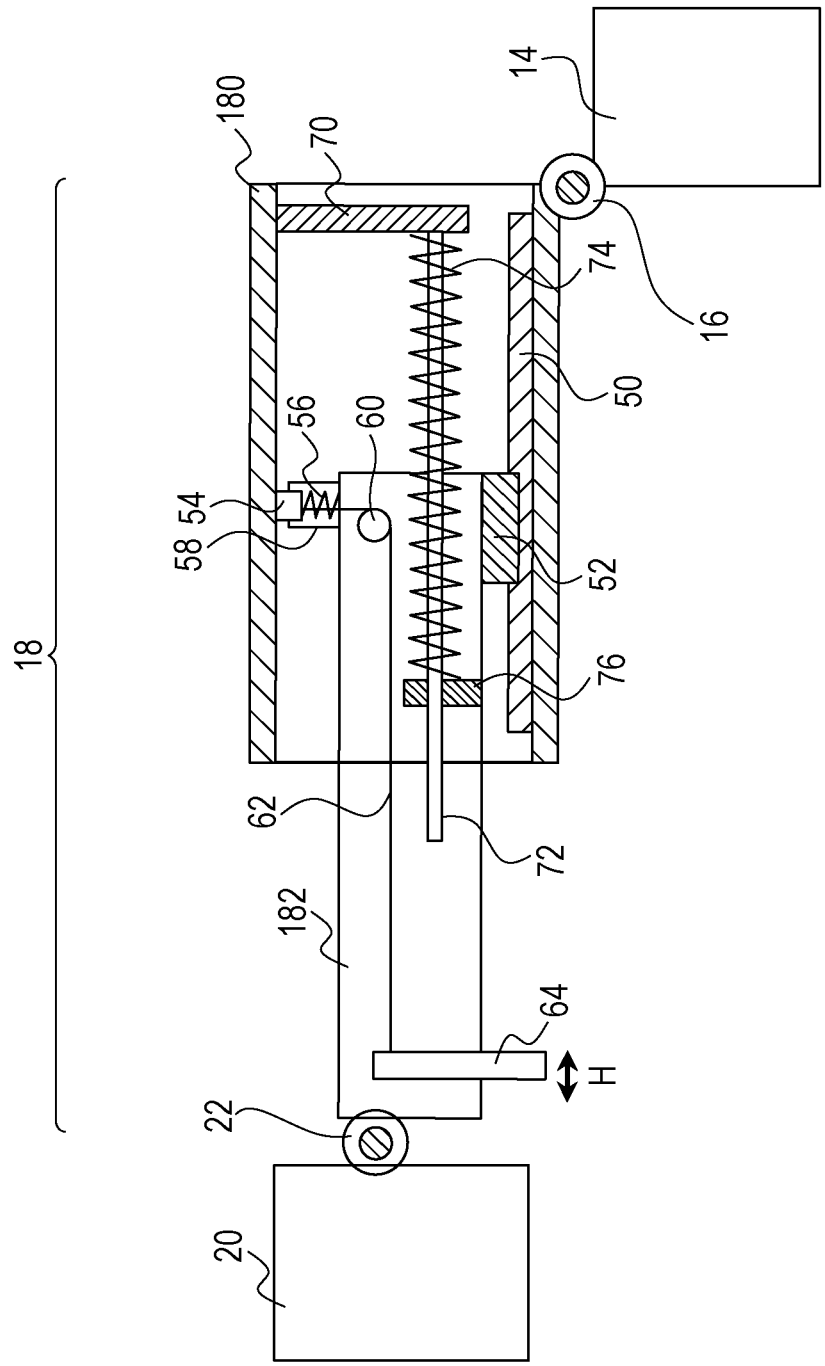
FIG. 7 is a drawing illustrating the expandable mechanism of the arm of the radiation generating apparatus of this disclosure.

FIG. 7 is a drawing illustrating an expandable mechanism of the arm of the radiation generating apparatus. FIG. 7 illustrates a cross section of the arm 18. In a state in which the arm 18 as illustrated in FIG. 7 extends horizontally, the height of the radiation generating unit 20 is in the vicinity of 1000 mm. In terms of a human scale, a range from 1000 mm to 1600 mm is desirable as the height at which the operation of the radiation generating unit 20 is performed for achieving a good operability because the operator does not have to crouch his or her back for the operation. In other words, the compression force of the spring member 74 is desirably designed in view of a case where the arm 18 is moved upward from the horizontal position so that the radiation generating unit 20 is positioned above at a height on the order of 1600 mm.

The spring member 74 will be described further in detail. First of all, when the arm 18 is in the inclined state as illustrated in FIG. 6, weights of the radiation generating unit 20, the rotating portion 22, the movable arm 182 and components included in the movable arm 182 are applied to the spring member 74. At least the weights of the radiation generating unit 20 and the movable arm 182 are applied to the spring member 74. In other words, a component force of the weight of the components that are moved by the expansion or contraction of the arm 18 in the direction of inclination is applied to the spring member 74.

Generally, the operating force that expands and contracts the arm 18 is preferably set not to exceed a predetermined value (for example, 20 N or lower), which corresponds to an operating force that allows the operator to operate effortlessly (for example, 20 N or lower). Therefore, the force of the spring member 74 is preferably set to a value obtained by subtracting a predetermined value (for example, 20 N) from a component force of the weight of the components applied to the spring member 74 in the direction of inclination around the position at which the arm 18 is expanded to the limit.

Subsequently, as illustrated in FIG. 7, when the arm 18 is in the horizontal state, at least, the weight of the components of the radiation generating unit 20 and the movable arm 182 are not applied to the spring member 74. Therefore, the arm 18 is expanded by the force of the spring member 74. At this time, although the expansion of the arm 18 is allowed by releasing the lock release handle 64, contraction of the arm 18 cannot be achieved unless a force against the expansion of the spring member 74 is applied.

Accordingly, as described above, the operating force for contracting the arm 18 is preferably set not to exceed a predetermined value (for example, 20 N or lower) that allows the operator to operate effortlessly. Accordingly, in a state in which the arm 18 extends horizontally, a force of the spring member 74 in a state in which the arm 18 is contracted to the limit is preferably set to a predetermined value (for example, 20 N).

A spring multiplier of the spring member 74 is set so as to allow the operator to expand and contract the movable arm 182 effortlessly. For example, the spring multiplier of the spring member 74 is set on the basis of the weight of the components that are moved by expansion or contraction of the arm 18 and the angle of the arm 18. Specifically, the length from a base of the arm 18 to a distal end of the radiation generating unit 20 is preferable set to 1000 mm in view of folding with respect to the pillar 14 when the arm 18 is contracted. In view of a usage at a bed of ICU, a bed height of 1000 mm is assumed, and SID 1000 mm, which is a distance between a focal point of the radiation generating unit 20 and a detecting device that detects radiation, is assumed. Consequently the height of the radiation generating unit 20 needs to be set to 2000 mm. Therefore, in order to move the radiation generating unit 20 to the center of a general bed width 1000 mm, the length from the base of the arm 18 to the distal end of the radiation generating unit 20 in the state in which the arm 18 extends horizontally needs 1200 mm in view of the height 1000 mm. In other words, the expandable stroke of the arm 18 is preferably a length on the order of 200 mm.

Accordingly, the inclination of the arm 18 in the state of being expanded to the limit when the radiation generating unit 20 is at a height of 1600 mm is 30°. Assuming that the weight of the components moving by the expansion and contraction of the arm 18 described above is 6.0 kg, a maximum force applied to the spring member 74 when the arm 18 is inclined is 3.0 kgF, which is a component force of 6.0 kgF in a direction of 30°. An adequate force of the spring member 74 when the length of the arm 18 is the shortest is 2.0 kgF, and an adequate force of the spring member 74 when the length of the arm 18 is the longest is 1.0 kgF. The spring constant of the spring member 74 is 0.005 kgF/mm from the expandable stroke of the arm 18, 200 mm.

In this manner, the compression force of the spring member 74 is set so that the arm extension operating force becomes a value close to a predetermined value (for example, 20 N) at the time when the radiation generating unit 20 is positioned above, and the arm 18 is inclined to the maximum at a height of the radiation generating unit 20 at least within a range from 1000 to 1600 mm where the expansion of the arm 18 is performed.

As regards the arm contraction operating force as well, the spring constant and the stroke of the spring member 74 are preferably set and selected within a range of a force that can push back the arm 18 manually irrespective of the inclination of the arm 18 at least between 1000 and 1600 mm in height of the radiation generating unit 20 within a range in which the contraction of the arm 18 is performed.

As described thus far, according to Example 1, the arm 18 configured to support the radiation generating unit 20 that generates radiation, the pillar 14 configured to rotatably support the arm 18, and the movable base 10 configured to support the pillar 14 and move on the floor surface are provided, and the arm 18 includes the expandable mechanism configured to expand and contract in the longitudinal direction of the arm 18. Therefore, the radiation generating unit may be installed at arbitrary positions.

In this manner, according to the expandable mechanism of the arm 18 and the folding mechanism with respect to the pillar 14, a compact size suitable for mounting on the vehicle at the time of transportation is achieved. With the expandable mechanism of the arm 18, an apparatus having a large movable range of the radiation generating unit 20 is achieved.

Example 2

Figure 8:
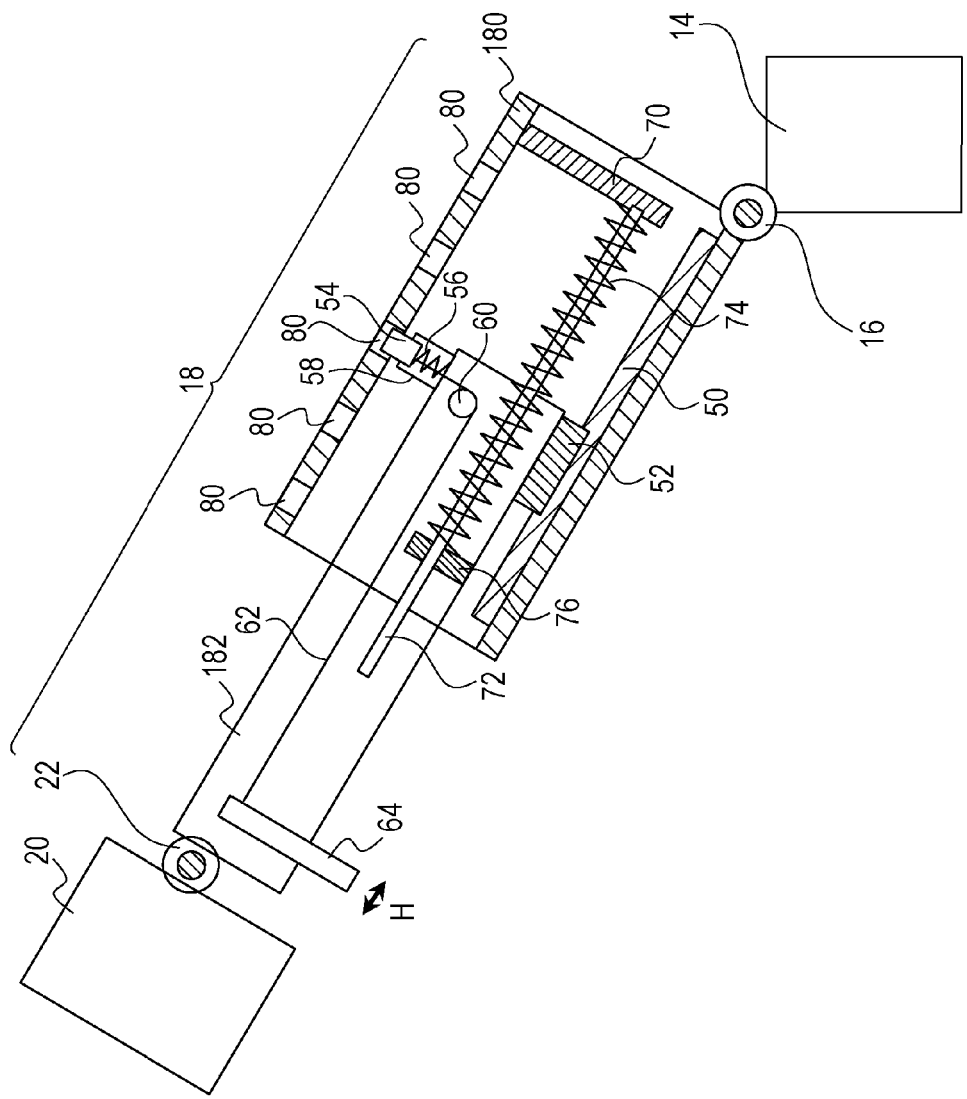
FIG. 8 is a drawing illustrating the radiation generating apparatus of Example 2 of this disclosure.
Figure 9:
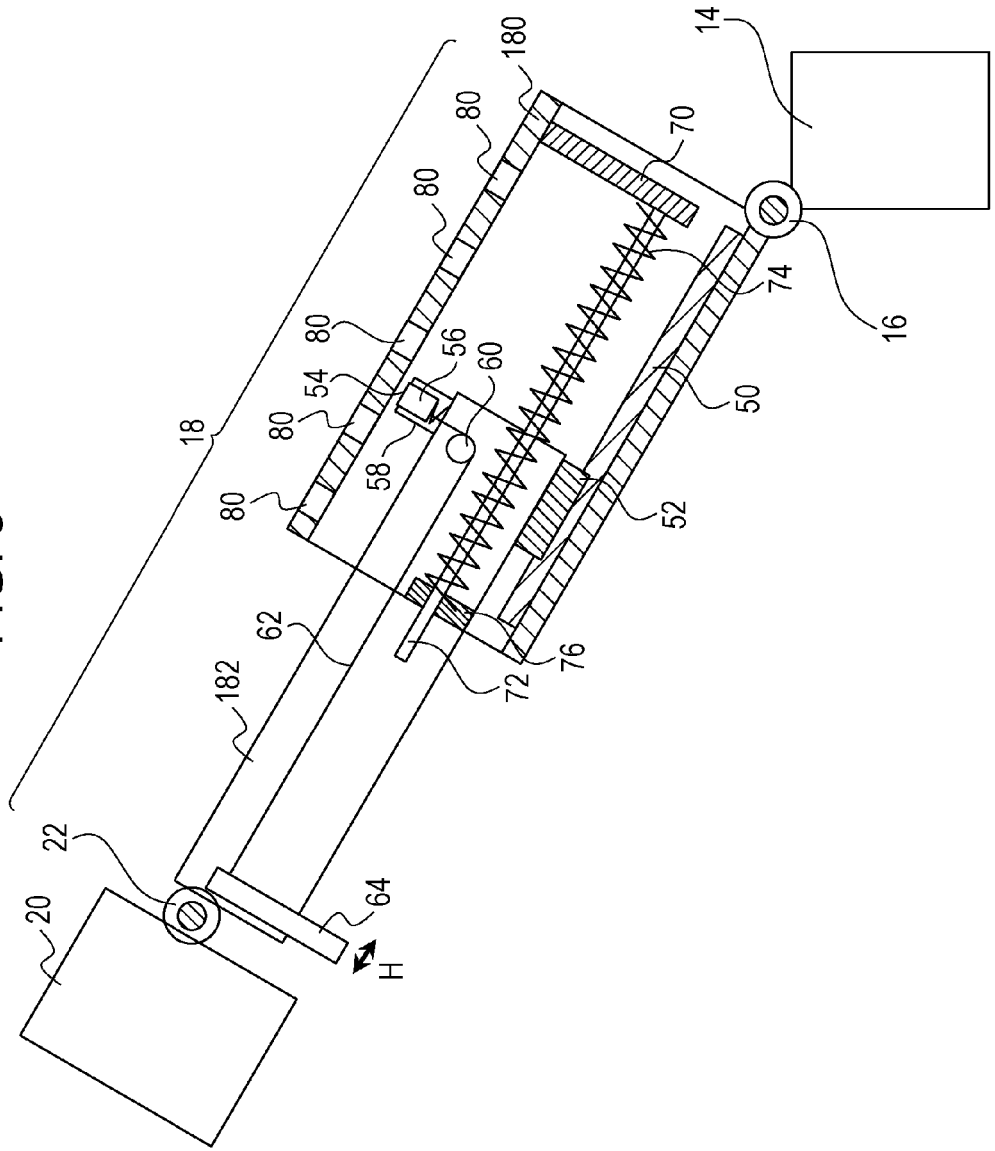
FIG. 9 is a drawing illustrating the radiation generating apparatus of Example 2 of this disclosure.

FIGS. 8 and 9 are drawings for explaining the radiation generating apparatus of Example 2. FIGS. 8 and 9 both illustrate a cross section of the arm 18. A different point from Example 1 is that the arm 18 has a plurality of hole portions 80 and a fixing mechanism configured to fix the arm 18 by the lock member 54 fitted in the hole portions 80. Here, only points different from Example 1 will be described.

The fixed arm 180 includes the plurality of hole portions 80 for fixing the position of the movable arm 182. Specifically, the plurality of hole portions 80 are arranged inside the fixed arm 180 on surfaces of the movable arm 182 opposing the slide guide 58 (the lock member 54).

The plurality of hole portions 80 each have a shape that allows the lock member 54 to fit therein. In the mode in which the lock member 54 is fitted in the hole portions 80, the plurality of hole portions 80 is larger than the lock member 54 in size. The shape of the plurality of hole portions 80 is preferably the same shape as the lock member 54.

The plurality of hole portions 80 are arranged on a trajectory of the lock member 54 when the arm 18 is expanded and contracted. In other words, the plurality of hole portions 80 are arranged inside the fixed arm 180 along the direction of expansion and contraction of the movable arm 182, that is, in the longitudinal direction of the fixed arm 180.

As illustrated in FIG. 8, when the lock member 54 is fitted in one of the plurality of hole portions 80, the movable arm 182 is restricted from moving and is fixed. Since the lock member 54 is pressed against the inside of the fixed arm 180 by the compression spring 56, when there is the hole portion 80 on the side opposing the lock member 54, the lock member 54 is pressed toward the hole portion 80 and is fitted in the hole portions 80.

As described in Example 1, the lock release handle 64 can be slid in the longitudinal direction (direction H) of the movable arm 182 as illustrated in FIG. 9. By releasing the lock by the lock member 54 by the lock release handle 64, the movable arm 182 is allowed to move. In other words, the arm 18 may be expanded and contracted.

In Example 1, the lock member 54 comes into contact with the inside of the fixed arm 180 to restrict the movement of the movable arm 182. However, in Example 2, the lock member 54 is fitted in the hole portions 80 of the fixed arm 180, the movement of the movable arm 182 is restricted. The mode of Example 2 restricts the movement of the movable arm 182 more strongly than the mode of Example 1.

By having a plurality of hole portions 80, even though the wire 62 is broken, the movable arm 182 is prevented from coming apart from the fixed arm 180. Therefore, the radiation generating apparatus that maintains the safety of the operator is provided.

The plurality of hole portions 80 are preferably arranged so as to have a hole interval not more than a predetermined interval (for example, 30 mm). Accordingly, even though the wire 62 is broken accidentally without the intention of the operator, the expanding and contracting movements of the movable arm 182 may be reduced. The hole interval may be changed by clogging or opening some of the plurality of hole portions 80.

Although the mode having five of the hole portions 80 is illustrated on the fixed arm 180, the number of the hole portions 80 is not limited as long as two or more are provided.

Example 3

Figure 10:
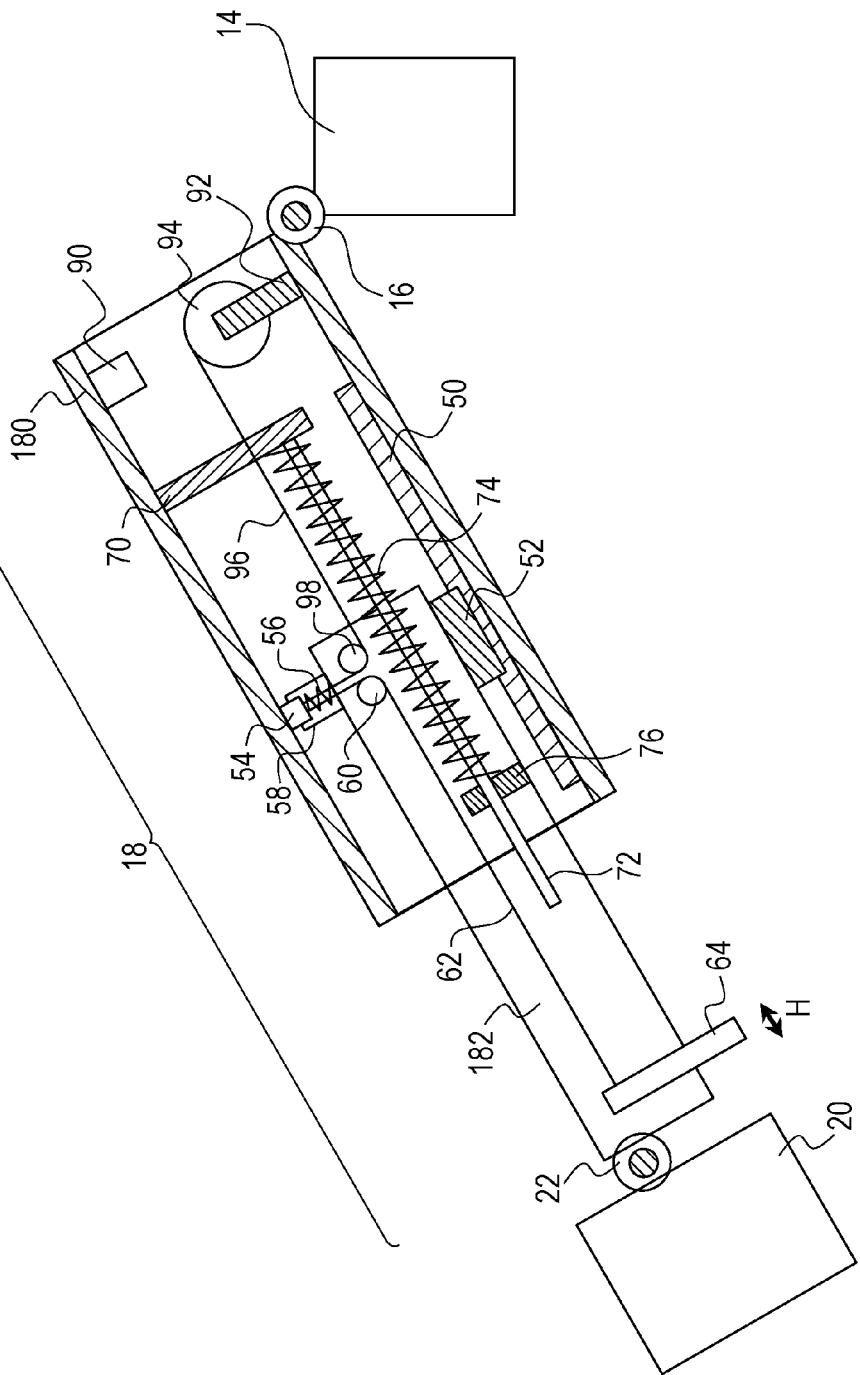
FIG. 10 is a drawing illustrating the radiation generating apparatus of Example 3 of this disclosure.
Figure 11:
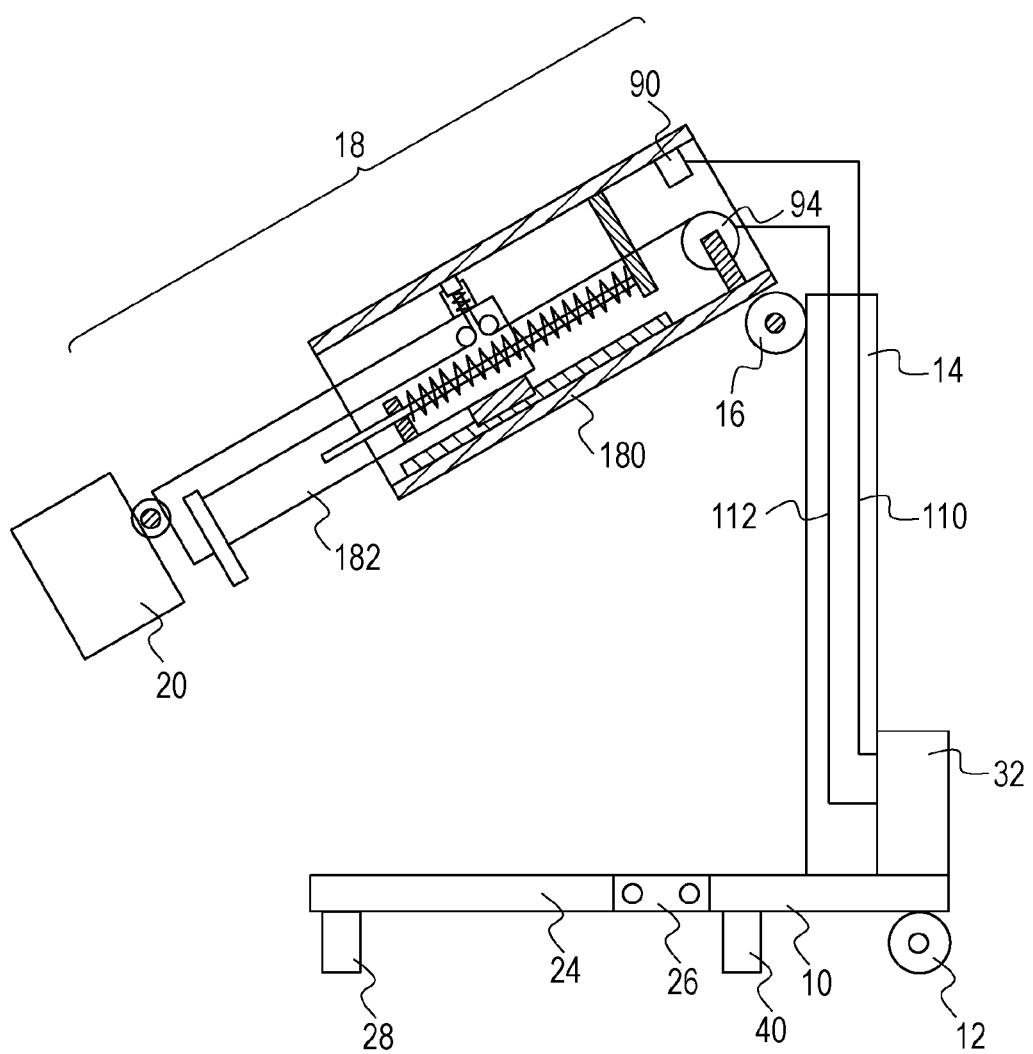
FIG. 11 is a drawing illustrating the radiation generating apparatus of Example 3 of this disclosure.
Figure 12:
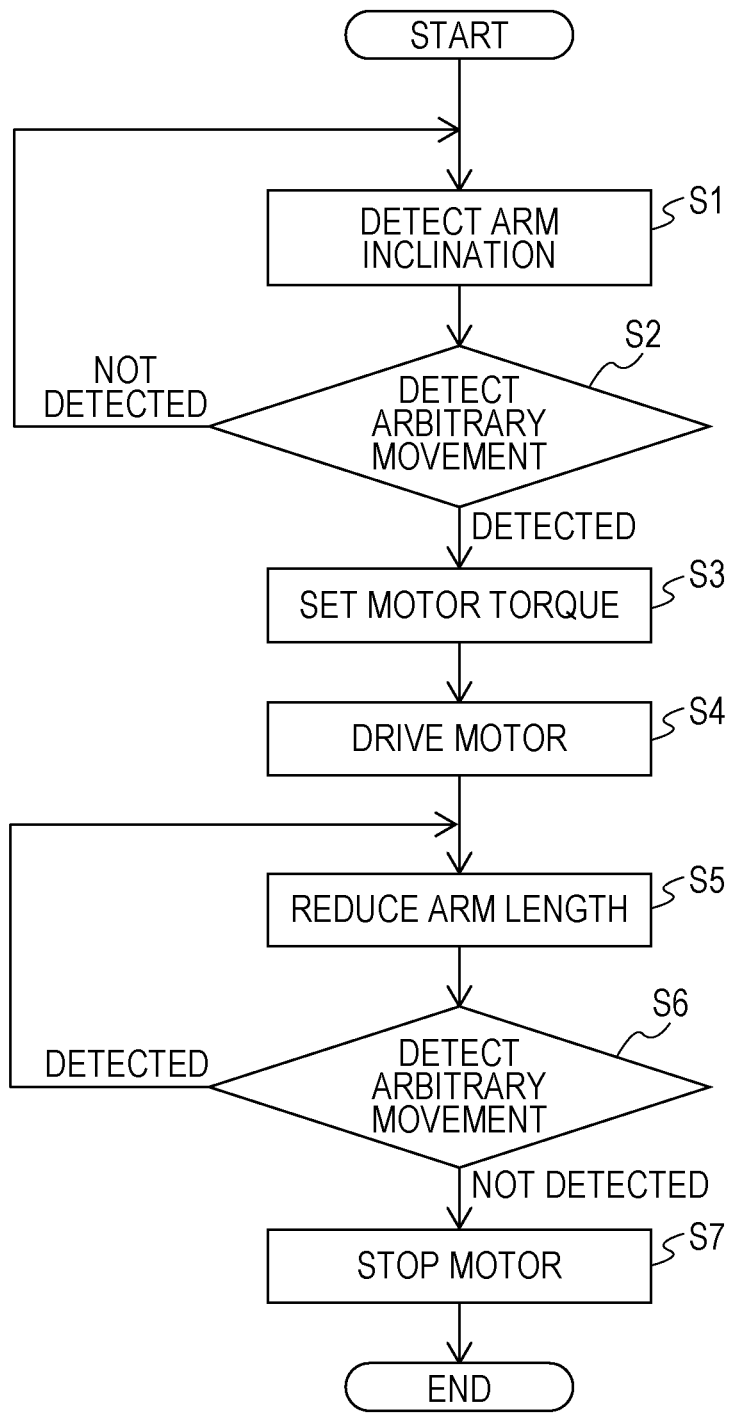
FIG. 12 is a flowchart illustrating an exemplary operation process of the radiation generating apparatus of this disclosure.

FIGS. 10 to 12 are drawings for explaining the radiation generating apparatus of Example 3. FIGS. 10 and 11 both illustrate a cross section of the arm 18. A different point from Examples 1 and 2 is that a sliding portion configured to cause the movable arm 182 to slide on the basis of the angle of inclination of the arm 18. Here, only points different from Examples 1 and 2 will be described.

In Example 3, a contracting operation of the arm 18 when the arm 18 is inclined to a level lower than the horizontal position is considered in Example 1, and a range of application is broadened.

The arm 18 includes an inclination sensor 90 configured to detect an inclined state of the arm 18. Specifically, the inclination sensor 90 is installed in the fixed arm 180 as illustrated in FIG. 10. The inclination sensor 90 may be installed in the movable arm 182.

The sliding portion includes at least a wire 96 configured to allow the movable arm 182 to be expanded and contracted, and a wire winding portion 94 configured to wind the wire 96. The wire winding portion 94 includes a motor in the interior thereof.

Specifically, a supporting portion 92 configured to rotatably fix the wire winding portion 94 inside the fixed arm 180 is provided. The movable arm 182 is provided with a pulley 98 installed thereon. The wire 96 is coupled to the lock member 54 and the wire winding portion 94 via the pulley 98. The wire 96 coupled to the wire winding portion 94 reaches the pulley 98 along the longitudinal direction of the fixed arm 180 and the movable arm 182, and the direction of the wire 96 is changed by the pulley 98. In the movable arm 182, a portion where the movable arm 182 and the slide guide 58 come into contact with each other includes a hole portion which allows the wire 96 to pass through. The wire 96 is bent in the direction orthogonal to the direction of the axis of the movable arm 182 by the pulley 98, and is coupled to the lock member 54. Accordingly, the wire winding portion 94 and the lock member 54 are interlocked with each other.

When the wire 96 is wound by the wire winding portion 94, the lock member 54 is pulled and the pressing of the lock member 54 against the fixed arm 180 is eliminated. The lock member 54 is no longer in contact with the inside of the fixed arm 180, the arm 18 is then free to expand and contract. When the wire 96 is further wound by the wire winding portion 94, the length of the wire 96 between the wire winding portion 94 and the pulley 98 is reduced, and the movable arm 182 can be contracted. When the wire winding portion 94 is not driven, the brake is not applied or the power is not transmitted.

In Example 3, a given action detecting unit, which is not illustrated, is provided. The action detecting unit is preferably provided as a push-button switch in the vicinity of the lock release handle 64 in terms of an improvement of operability. The winding of the wire 96 by the wire winding portion 94 is started by ON and OFF of the push-button switch.

FIG. 11 is a control block diagram illustrating the radiation generating apparatus of Example 3. The control unit 32 is electrically connected to the inclination sensor 90 configured to detect the state of inclination of the arm 18, the wire winding portion 94, and the given action detecting unit, which is not illustrated, via wires or wireless. A computer program which implements a function of the radiation generating apparatus of Example 3 (to slide the movable arm 182 on the basis of the angle of inclination of the arm 18) may be supplied to a computer via a network or a computer readable storage medium (which is not illustrated) to cause the computer program to be executed. In other words, the computer program is a program for implementing the function of an image processing apparatus by a computer. The computer readable storage medium stores the computer program.

The inclination sensor 90 outputs the state of inclination of the arm 18 to the control unit 32. The control unit 32 controls the wire winding portion 94 configured to wind the wire 96 on the basis of the state of inclination of the arm 18. For example, when the arm 18 is inclined to a level lower than the horizontal level, the wire winding portion 94 is controlled to wind the wire 96.

FIG. 12 is a flowchart illustrating actions of Example 3.

In Step S1, in association with startup or a preparation for photography of the radiation generating apparatus, the inclination sensor 90 detects the angle of inclination of the arm 18. The inclination sensor 90 then transmits the angle of inclination of the arm 18 to the control unit 32.

In Step S2, whether or not a given action by the operator is performed, for example, whether or not the push button is pressed, is determined by a given action detecting unit. The given action detecting unit transmits operation information of the operator to the control unit 32. When the operation of the operator is not detected, the procedure goes back to Step S1, and when the operation of the operator is detected, the procedure goes to Step S3.

In Step S3, the control unit 32 sets a torque value of the motor in the wire winding portion 94 corresponding to the angle of inclination of the arm 18. The control unit 32 has a table in which the torques values corresponding to the angles of inclination are stored in advance. For example, when the angle of inclination of the arm 18 is large, the torque value is set to a large value, and when the angle of inclination of the arm 18 is small, the torque value is set to a small value. The control unit 32 sets a torque value of the motor on the basis of the stored table.

In Step S4, by driving the motor of the wire winding portion 94, the wire 96 is wound and the expansion lock of the arm 18 by the lock member 54 is released.

In Step S5, the wire 96 is wound to pull the movable arm 182 into the movable arm 182. Considering to collapse of the compression spring 56, a stopper may be provided so that the lock member 54 stops at a position in the slide guide 58 where no collapse of the compression spring 56 occurs.

Subsequently, the procedure goes to Step S6, and an action is detected again by the given action detecting unit. When no action is detected, the procedure goes back to Step S5, and the procedure goes to Step S7 when an action is detected.

In Step S7, the drive of the motor of the wire winding portion 94 is stopped, and the rotation of the wire winding portion 94 is set to be free. The lock member 54 is pressed against the inside of the fixed arm 180, and the expansion and contraction of the arm 18 is locked. A configuration including a sensor configured to detect the fact that the arm 18 is contracted to the maximum and a unit configured to stop the motor of the wire winding portion 94 on the basis of the detection by the sensor is also applicable.

With the configuration described thus far, the operating force required for contracting the arm 18 may be reduced irrespective of the angle of inclination of the arm 18, and the radiation generating apparatus superior in operability which provides ease of expansion and contraction of the arm 18 may be provided.

The radiographing apparatus of this disclosure includes the radiation generating apparatus, and, although not illustrated, a detecting device configured to detect radiation passing through the object and output image data according to radiation, and a display apparatus configured to display images.

Radiation includes not only α beams, β beams, γ beams, X rays, which are beams forming particles (including photon) emitted by radioactive decay but also beams having energy equivalent thereto or more, for example, particle rays or cosmic rays.

The supporting platform 24 in the radiographing apparatus of this disclosure has been described as being a plate-shaped member. However, the supporting platform 24 is not limited thereto, and may be any types of member as long as it has a predetermined rigidity, and is foldable with respect to the movable base 10. For example, a member composed of a plurality of rods, a mesh-like member, a member having a curved surface may also be applied.

Although the arm 18 and the pillar 14 of the radiographing apparatus of this disclosure have been described as being separate members, this disclosure is not limited to the arm 18 and the pillar 14, and one supporting mechanism having functions of the arm 18 and the pillar 14 is also applicable. The supporting mechanism is a member having a mechanism that couples the radiation generating unit 20 and the movable base 10, and configured to support the radiation generating unit 20 and be expandable. The supporting mechanism has a mechanism to apply a force in the direction of expansion.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-073016, filed Mar. 29, 2013, which is hereby incorporated by reference herein in its entirety.

What is claimed is:

1. A radiation generating apparatus comprising:
an arm configured to support a radiation generating unit that generates radiation;
a pillar configured to rotatably support the arm; and
a movable base configured to support the pillar and move on a floor surface,
wherein the arm includes an expandable mechanism configured to expand and contract in a longitudinal direction of the arm, and
wherein the arm includes a biasing mechanism configured to reduce an operating force required by an operator for expanding and contracting the arm.

2. The radiation generating apparatus according to claim 1, wherein the biasing mechanism is a mechanism configured to apply a force in a direction of expansion of the arm.

3. The radiation generating apparatus according to claim 1, wherein the arm includes a fixed arm and a movable arm configured to be movable with respect to the fixed arm, and the biasing mechanism includes a spring member coupled to the movable arm and the fixed arm.

4. The radiation generating apparatus according to claim 3, further comprising spring fixing portions,
wherein a first spring fixing portion configured to fix one end of the spring member is installed inside the fixed arm, and a second spring fixing portion configured to fix the other end of the spring member is installed inside the movable arm.

5. The radiation generating apparatus according to claim 4, further comprising a spring shaft,
wherein the spring shaft of the spring member is installed so as to be fixed to the first spring fixing portion installed on the fixed arm together with the spring member, and penetrates through the second spring fixing portion installed on the movable arm.

6. The radiation generating apparatus according to claim 5, wherein at least weights of the radiation generating unit and the movable arm are applied to the spring member.

7. The radiation generating apparatus according to claim 6, wherein a spring multiplier of the spring member is set on the basis of the weights of the components that are moved by expansion or contraction of the arm 18 and an angle of the arm.

8. The radiation generating apparatus according to claim 1, wherein the arm includes a fixed arm section and a movable arm section configured to be movable with respect to the fixed arm section.

9. The radiation generating apparatus according to claim 8, wherein the movable arm includes a slide guide for positioning the movable arm.

10. The radiation generating apparatus according to claim 9, wherein the slide guide includes a lock member configured to restrain and lock the movement of the movable arm by coming into contact with the inside of the fixed arm, and a compression spring configured to press the lock member against the inside of the fixed arm.

11. The radiation generating apparatus according to claim 10, wherein the movable arm includes a lock release handle configured to release the lock by the lock member.

12. The radiation generating apparatus according to claim 10, wherein the arm includes a plurality of hole portions, and a fixing mechanism configured to fix the arm by the lock member fitted in the hole portions.

13. The radiation generating apparatus according to claim 8, comprising a sliding portion configured to slide the movable arm on the basis of the angle of inclination of the arm.

14. The radiation generating apparatus according to claim 1, including a supporting platform foldable with respect to the movable base.

15. The radiation generating apparatus according to claim 1, wherein the radiation generating unit is a transmissive radiation generating unit.

16. The radiation generating apparatus according to claim 1, further comprising a rotating portion including a swivel hinge configured to rotate the radiation generating unit about an axis parallel to a longitudinal direction of the arm, and a tilt hinge configured to rotate the radiation generating unit about an axis perpendicular to the longitudinal direction of the arm.

17. A radiographing apparatus comprising the radiation generating apparatus according to claim 1, a detecting device configured to detect radiation passing through an object and output image data according to radiation, and a display apparatus configured to display the image.

18. A process of controlling a radiation generating apparatus, the apparatus including a movable arm configured to support a radiation generating unit that generates radiation; a pillar configured to rotatably support the movable arm; and driving motor configured to move the movable arm on the basis of an angle of inclination of the arm, the process comprising:
   detecting the angle of inclination of the movable arm;
   determining movement of the movable arm;
   setting a torque amount to the driving motor corresponding to the angle of inclination; and
   driving the movable arm using the amount of torque.

19. A computer readable storage medium storing a program for causing a computer to implement the process according to claim 18.

20. A radiation generating apparatus comprising:
   an arm configured to support a radiation generating unit that generates radiation;
   a pillar configured to rotatably support the arm; and
   a movable base configured to support the pillar and move on a floor surface,
   wherein the arm includes an expandable mechanism configured to expand and contract in a longitudinal direction of the arm, and
   wherein the arm includes a biasing mechanism configured to apply a force in a direction of expansion of the arm.

21. A radiation generating apparatus comprising:
   an arm configured to support a radiation generating unit that generates radiation;
   a pillar configured to rotatably support the arm; and
   a movable base configured to support the pillar and move on a floor surface,
   wherein the arm includes an expandable mechanism configured to expand and contract in a longitudinal direction of the arm,
   wherein the arm includes a fixed arm section and a movable arm section configured to be movable with respect to the fixed arm section, and
   wherein the movable arm includes a lock member configured to lock the movement of the movable arm by contacting with the fixed arm and a lock release handle configured to release the lock by the lock member.

* * * * *